US005733870A

United States Patent [19]

Alm

[11] Patent Number: 5,733,870
[45] Date of Patent: Mar. 31, 1998

[54] OINTMENT FOR TREATMENT OF EPITHELIAL LESIONS

[75] Inventor: Per Alm, deceased, late of Hornefors, Sweden, by Pia Alm, heiress

[73] Assignee: ProCell Bioteknik i Hornefors AB, Sweden

[21] Appl. No.: 131,149

[22] Filed: Oct. 4, 1993

[30] Foreign Application Priority Data

Oct. 5, 1992 [SE] Sweden .................. 9302895

[51] Int. Cl.$^6$ .................. A61K 38/17; A61K 38/39
[52] U.S. Cl. .................. 514/8; 514/2
[58] Field of Search .................. 514/8, 2

[56] References Cited

U.S. PATENT DOCUMENTS

| | | | |
|---|---|---|---|
| 4,017,615 | 4/1977 | Shastri et al. | 424/241 |
| 4,837,019 | 6/1989 | Georgalas et al. | 424/101 |
| 4,849,406 | 7/1989 | Salonen | 514/8 |
| 4,939,135 | 7/1990 | Robertson et al. | 514/179 |
| 4,983,385 | 1/1991 | Hasegawa et al. | 424/78 |
| 5,036,056 | 7/1991 | Kludas | 514/54 |
| 5,053,388 | 10/1991 | Gibson et al. | 514/2 |
| 5,055,298 | 10/1991 | Kludas | 424/401 |
| 5,196,185 | 3/1993 | Silver et al. | 424/45 |
| 5,246,708 | 9/1993 | von Borstel et al. | 424/450 |

OTHER PUBLICATIONS

Kim, KS et al., "Topical fibronectin treatment in persistent corneal epithelial defects . . . ", Korean J. of Opthalmol. (1990 Jun.) vol. 4(1), pp. 5–11.
The U.S. Pharmocopeia, USP XXI, pp. 1491–1493, 1992.

Primary Examiner—Chhaya D. Sayala
Attorney, Agent, or Firm—Ostrolenk, Faber, Gerb & Soffen, LLP

[57] ABSTRACT

An ointment containing fibronectin for treatment of epithelial lesions in animals comprises between 0.00001% by weight and 0.1% by weight species-specific fibronectin, between 17 and 45% by weight of vaselinum album, between 5 and 15% by weight of cetostearyl alcohol, between 5 and 12 g by weight of polysorbate and at least 30% by weight of water.

16 Claims, No Drawings

OINTMENT FOR TREATMENT OF EPITHELIAL LESIONS

The present invention relates to an ointment containing fibronectin for treatment of epithelial lesions in animals including man.

Fibronectin is a normal plasma and extracellular matric glycoprotein. Its wound-healing effect is well known. Fibronectin has been incorporated into a number of cosmetic compositions and into pharmaceutical preparations to promote wound healing or treating skin conditions that, if untreated, may result in wounds.

An eye drop composition containing aprotinin and fibronectin is disclosed in EP-A- 223 254. This known composition promotes healing of plasmin-induced epithelial lesions produced by plasmin present in tear fluids.

U.S. Pat. No. 4,837,019 discloses a skin treatment composition, e.g. a cream, which counteracts moisture loss and promotes healing of burned or sunburned skin comprising water and 2–30% by weight of a moisturizing component mixture containing, i.a. polyglyceryl methacrylate, glycerine, allantoin, panthenol, fibronectin and an aminoacid complex including proline, arginine and pyrrolidine carboxylic acid.

U.S. Pat. No. 4,734,279 discloses a therapeutic composition, particularly a drug, containing immunoglobulins and an other pharmacological preparation containing antibiotics, interferon, antitrypsin, fibronectin, lysozyme and/or other components, enhancing by synergism the therapeutic effect of the immunoglobulins.

In a study of healing enhancement by fibronectin of excised wounds in rats (Cheng, C. Y. et al., *Arch. Dermatol.* 124 (1988) 221–225); the authors used a number of vehicles for exogeneous application of the glycoprotein: phosphate-buffered saline, dimethoxyl sulfoxide, Aquaphor® (Beiersdorf Inc.) Orabase® (Hoyt Labs), hydrophilic petrolatum, sepharose (Sepharose 4B, Pharmacia) and polyethylene glycol. The results obtained with the two inert ointment carriers, Aquaphor and Orabase, were disappointing. Aquaphor appeared to inhibit wound healing compared with the control phosphate-buffered saline while quite high concentrations of fibronectin (1000 µg/ml) were needed to demonstrate effect with Orabase. Aquaphor is an ointment base rich in hydrophobic components such as cholesterol, stearyl alcohol, petrolatum and waxes in mineral oil which makes achieving higher concentrations of fibronectin a problem whereas the main component of Orabase is water.

Polyethylene glycol was about as effective as Orabase as wound-healing vehicle for fibronectin. Sepharose showed discernable effect after 9 days of treatment and hydrophylic petrolatum after 11 days only.

From what is known in the art, it appears that fibronectin, in contrast to its established wound-healing effect when transported to the wound by body fluids, shows poor or, at best, moderate effect when administered topically. It also appears that such topical effect is obtained only with carriers that are rich in water and/or contain comparatively small amounts of hydrophobic ingredients. A problem with carriers or carrier systems that are rich in water is that they have a tendency to dry and are easily removed by water or sweat.

The aim of the present invention is to overcome these drawbacks and to provide an ointment for the treatment of wounds containing fibronectin that has good healing effect and is long-lasting.

According to the present invention, an ointment containing fibronectin and having good effect in wound treatment in animals including man comprises (a) between 0.00001% by weight and 0.1% by weight species-specific fibronectin, (b) between 17 and 45% by weight of a member of the group consisting of vaselinum album, a mixture of n-alkanes having essentially the same boiling range as vaselinum album and a mixture thereof, (c) between 5 and 15% by weight of cetyl alcohol, stearyl alcohol and cetostearyl alcohol, (d) between 5 and 12 g by weight of polysorbate and (e) at least 30% by weight of water.

It is preferred for the ointment to contain between 25 and 37% by weight, particularly preferred about 31% by weight, of a member of the group consisting of vaselinum album, a mixture of n-alkanes having essentially the same boiling range as vaselinum album and a mixture thereof.

It is further preferred for the ointment to contain between 7 and 11% by weight, particularly preferred about 9% by weight, of a member of the group consisting of cetyl alcohol, stearyl alcohol and cetostearyl alcohol.

It is also preferred for the ointment to contain between 2 and 15% by weight of polysorbate, preferably about 8% by weight.

According to an advantageous aspect of the invention, the ointment further contains one or several members of group consisting of liquid paraffin, in an amount of between 0 and 10% by weight, more preferred about 3% by weight, glycerol monostearate, in an amount of between 0 and 6% by weight, more preferred about 3% by weight, propylene glycol, in an amount of between 0 and 8% by weight, more preferred about 5% by weight, and neutral oil, in an amount of between 0 and 5% by weight, more preferred about 2% by weight.

According to another advantageous aspect of the invention, the ointment further comprises sorbate and/or silicic acid.

It is particularly advantageous for the ointment according to the invention to comprise vitamins, particularly vitamin A and vitamin D. The preferred water content of the ointment is about 40% by weight.

The ointment according to the invention may also contain other substances that are commonly used in formulating ointments for wound treatment, such as antibacterial, antiviral and antifungal agents, moisture controlling agents, emulsion stabilizing agents, antioxidants, UV-filtering agents, etc.

The invention will now be explained in more detail by reference to a number of non-limiting examples.

EXAMPLE 1

In a 0.3 l beaker 31 g of vaselinum album, 3 g of liquid paraffin, 8.5 g of cetostearyl alcohol, 7.5 g of polysorbate 40 (Tween® 40), 2 g of neutral oil (Myglyol® 812), 5 g polyethylene glycol and 3 g glycerol monostearate were melted and blended at 70° C., and emulgated with 40 g water. The mixture was cooled to 35° C. and combined with 0.4 ml of an aqueous solution containing 0.9% by weight of sodium chloride and 0.01% by weight equine fibronectin.

This procedure was repeated with human and bovine fibronectin, respectively.

EXAMPLE 2

Fibronectin (human, equine, bovine) was prepared according to Ruoslahti, E. et al Methods Enzymol. 82 (1982) 803.

EXAMPLE 3

Wound healing test on horse (laboratory conditions)

The ointment of Example 1 was tested on three horses (age 12+years). Under local anaesthesia, 4 symmetrically positioned sterile wounds, each having an area of 400 mm². were excised in the neck region. Wound 1 was treated with the active ointment, wound 2 with ointment not containing fibronectin, wound 3 with physiologic sodium chloride solution, wound 4 with a commercial ointment (Nelex®). The wounds were treated with the respective preparation twice per day. Healing progress was determined by measuring wound size. In all animals, the ointment of example 1 showed superior healing effect from the start. Nine days after the start, the average reduction in wound size was 53% for the ointment according to the invention and 36% for saline; the healing efficiency for the other preparations was inferior to that of saline.

EXAMPLE 4

Wound healing test on cattle (field conditions)

Thirty-four cows with a variety of wounds (udder, dug, flank, upper side of cloven-foot, burns, etc.) were treated with the ointment according to Example 1 (bovine fibronectin). The tests were carried out and the results assessed by a number of experienced veterinaries. In 31 cases, improved healing (shorter than expected healing time or superior wound area shrinkage) was reported. The ointment, however, seemed to lack effect against mastitis wounds.

During the field tests, the ointment showed good stability in rainy or damp weather. In contrast to ointments having a high water content, the ointment according to the invention has the further advantage of being applicable and stable at sub-zero temperatures.

we claim:

1. An ointment containing fibronectin for treatment of epithelial lesions in animals, characterized in that it consists essentially of (a) between 0.00001% by weight and 0.1% by weight species-specific fibronectin, (b) between 17 and 45% by weight of a member selected from the group consisting of vaselinum album, a mixture of n-alkanes having essentially the same boiling range as vaselinum album and a mixture thereof, (c) between 5 and 15% by weight of an agent selected from the group consisting of cetyl alcohol, stearyl alcohol and cetostearyl alcohol, (d) between 5 and 12% by weight of polysorbate and (e) at least 30% by weight of water.

2. Ointment according to claim 1, characterized in that it contains between 25 and 37% by weight of the member of the group consisting of vaselinum album, a mixture of n-alkanes having essentially the same boiling range as vaselinum album and a mixture thereof.

3. Ointment according to claim 2 characterized in that it contains about 31% by weight of component (b).

4. Ointment according to claim 1, characterized in that it contains between 7 and 11% by weight of the agent of the group consisting of cetyl alcohol, stearyl alcohol and cetostearyl alcohol.

5. Ointment according to claim 4, characterized in that it contains about 9% by weight of component (c).

6. Ointment according to claim 1, characterized in that it contains between 2 and 15% by weight of polysorbate.

7. Ointment according to claim 6, characterized in that it contains about 8% by weight of polysorbate.

8. Ointment according to claim 1, characterized in that it further contains liquid paraffin in an amount of between 0 and 10% by weight, glycerol monostearate in an amount of between 0 and 6% by weight propylene glycol in an amount of between 0 and 8% by weight, and neutral oil in an amount of between 0 and 5% by weight.

9. Ointment according to claim 7, characterized in that it contains about 3% liquid paraffin, about 3% glycerol monostearate, about 5% propylene glycol and about 2% neutral oil.

10. Ointment according to claim 7, characterized in that it contains about 31% by weight of the member (b), about 9% by weight of the agent (c), about 8% by weight of polysorbate, about 3% liquid paraffin, about 3% glycerol monostearate, about 5% propylene glycol and about 2% neutral oil.

11. In a method of the topical treatment of wounds in animals, utilizing the ointment of claim 10.

12. Ointment according to claim 1, characterized in that it further comprises vitamins.

13. Ointment according to claim 12, characterized in that the vitamins comprise at least one member of the group consisting of vitamin A and vitamin D.

14. Ointment according to claim 1, characterized in that it further comprises at least one of sorbate and silicic acid.

15. Ointment according to claim 1, characterized in that it contains about 40% by weight of water.

16. In a method of the topical treatment of wounds in animals, utilizing the ointment of claim 1.

* * * * *